(12) United States Patent
Nguyen et al.

(10) Patent No.: US 10,881,427 B2
(45) Date of Patent: Jan. 5, 2021

(54) SURGICAL CUTTING INSTRUMENT

(71) Applicant: MEDTRONIC-XOMED, INC., Jacksonville, FL (US)

(72) Inventors: Thoai Nguyen, Jacksonville, FL (US); Phillip J. Berman, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 250 days.

(21) Appl. No.: 15/958,130

(22) Filed: Apr. 20, 2018

(65) Prior Publication Data

US 2018/0235655 A1    Aug. 23, 2018

Related U.S. Application Data

(63) Continuation of application No. 14/689,938, filed on Apr. 17, 2015, now Pat. No. 10,022,144.

(51) Int. Cl.
*A61B 17/3207* (2006.01)
*A61B 17/32* (2006.01)
(Continued)

(52) U.S. Cl.
CPC ......... *A61B 17/320783* (2013.01); *A61B 17/32002* (2013.01); *A61B 17/320758* (2013.01);
(Continued)

(58) Field of Classification Search
CPC ........ B23D 75/00; B23D 27/00; B23D 27/02; B23D 27/04; B23D 27/06; B23D 75/005;
(Continued)

(56) References Cited

U.S. PATENT DOCUMENTS 4,167,943 A    9/1979    Banko
4,646,738 A    3/1987    Trott
(Continued)

FOREIGN PATENT DOCUMENTS

JP    2000-508206    7/2000
JP    2003-524479    8/2003
(Continued)

OTHER PUBLICATIONS

International Search Report and Written Opinion of the International Searching Authority, dated Jun. 16, 2016, 15 pages.

*Primary Examiner* — Thomas McEvoy
(74) *Attorney, Agent, or Firm* — Dicke, Billig & Czaja, PLLC

(57) ABSTRACT

A surgical cutting instrument including a first tubular member, a second tubular member, a sleeve member, a third tubular member, and an orientation member. The first tubular member includes a cutting tip. The second tubular member has a distal region forming a cutting window. The first tubular member is co-axially disposed within the second tubular member such that the cutting tip is selectively exposed at the cutting window. The first and second tubular members are co-axially disposed within the sleeve member. The third tubular member is co-axially disposed around an intermediate section of the first tubular member, an intermediate region of the second tubular member and the sleeve member. The orientation member is rotatable to transmit a rotational force applied to the orientation member to selectively rotate the second and third tubular members relative to the sleeve member to effectuate spatial rotation of the cutting window.

17 Claims, 6 Drawing Sheets

(51) Int. Cl.
*A61B 17/00* (2006.01)
*A61B 17/29* (2006.01)

(52) U.S. Cl.
CPC ............... *A61B 2017/00455* (2013.01); *A61B 2017/2929* (2013.01); *A61B 2017/320032* (2013.01); *A61B 2017/320064* (2013.01)

(58) Field of Classification Search
CPC .................. B23D 77/00; B23D 67/12; A61B 17/320783; A61B 17/32002; A61B 17/320758; A61B 2017/320032; A61B 2017/00455; A61B 2017/320064
See application file for complete search history.

(56) References Cited

U.S. PATENT DOCUMENTS

| | | |
|---|---|---|
| 4,811,736 A | 3/1989 | Griggs et al. |
| 4,850,354 A | 7/1989 | McGurk-Burleson et al. |
| RE33,258 E | 7/1990 | Onik et al. |
| 4,986,827 A | 1/1991 | Akkas et al. |
| 5,152,744 A | 10/1992 | Krause et al. |
| 5,275,609 A | 1/1994 | Pingleton et al. |
| 5,409,013 A | 4/1995 | Clement |
| 5,411,514 A | 5/1995 | Fucci et al. |
| 5,601,583 A | 2/1997 | Donahue et al. |
| 5,620,447 A | 4/1997 | Smith et al. |
| 5,643,304 A | 7/1997 | Schechter et al. |
| 5,669,876 A | 9/1997 | Schechter et al. |
| 5,685,840 A | 11/1997 | Schechter et al. |
| 5,709,698 A | 1/1998 | Adams et al. |
| 5,782,795 A | 7/1998 | Bays |
| 5,833,692 A | 11/1998 | Cesarini et al. |
| 6,183,433 B1 | 2/2001 | Bays |
| 6,620,180 B1 | 9/2003 | Bays et al. |
| 6,638,289 B1 | 10/2003 | Johnson et al. |
| 8,070,765 B2 | 12/2011 | Oliver et al. |
| 8,202,288 B2 | 6/2012 | Adams et al. |
| 8,409,235 B2 | 4/2013 | Rubin |
| 2005/0277970 A1 | 12/2005 | Norman et al. |
| 2006/0200123 A1 | 9/2006 | Ryan |
| 2009/0234378 A1* | 9/2009 | Escudero ....... A61B 17/320758 606/180 |
| 2009/0270894 A1 | 10/2009 | Rubin et al. |
| 2010/0152761 A1 | 6/2010 | Mark |
| 2010/0298763 A1 | 11/2010 | Adams et al. |
| 2012/0109172 A1 | 5/2012 | Schmitz et al. |
| 2012/0157879 A1 | 6/2012 | Mark et al. |
| 2013/0012972 A1 | 1/2013 | Norman et al. |

FOREIGN PATENT DOCUMENTS

| | | |
|---|---|---|
| JP | 2008-500106 | 1/2008 |
| WO | 01/22889 | 4/2001 |
| WO | 2005/117720 | 12/2005 |
| WO | 2013052963 A1 | 4/2013 |
| WO | 2014133644 A1 | 9/2014 |

* cited by examiner

SURGICAL CUTTING INSTRUMENT

CROSS-REFERENCE TO RELATED APPLICATIONS

This application is a continuation of U.S. application Ser. No. 14/689,938, filed Apr. 17, 2015, entitled "Surgical Cutting Instrument"; the entire teachings of which are incorporated herein by reference.

BACKGROUND

The present invention relates to a surgical cutting instrument. More particularly, it relates to a surgical cutting instrument adapted to facilitate cutting window rotation.

Surgical cutting instruments in which an elongate inner member is rotated within an elongate outer tubular member have become well accepted in surgical procedures where access to the surgical site is gained via a narrow portal or passage. Typically, the outer tubular member includes a distal end with an opening defining a cutting port or window, and the inner member includes a distal end forming a cutting tip for cutting bodily tissue at the window. Proximal ends of the inner and outer members are commonly secured to hubs that, in turn, are attached to a powered handpiece for rotating and/or oscillating the inner member relative to the outer tubular member. The cutting tip of the inner member can have various configurations specific to the surgical procedure in question (e.g., cutting, resecting, abrading, shaving, etc.), with the cutting window being suitably configured to cooperate with the particular configuration of the cutting tip. Often, the inner member is tubular so that the loose tissue resulting from a cutting, resecting, or abrading procedure can be aspirated through the hollow lumen of the inner member.

Use of the above-described surgical cutting instruments generally entails delivering the cutting window/cutting tip to the target site and positioning the cutting window such that the cutting tip is "exposed" to the desired tissue. To this end, with conventional surgical cutting instruments, while the inner member, and thus the cutting tip, is rotatable relative to the handpiece, the outer tubular member, and thus the cutting window, is not. That is to say, a rotational or spatial position of the cutting window relative to the handpiece is fixed with most available surgical cutting instruments. As a result, in order to spatially position the cutting window so as to expose the cutting tip to desired tissue, the surgeon must physically move or rotate the handpiece. In many instances, this requires the surgeon to contort his or her hand(s) to an otherwise uncomfortable position. Further, many surgical procedures require that tissue at different spatial locations at a particular target site be acted upon by the cutting tip. Thus, while upon initial placement at the target site the cutting window may be properly oriented for a first portion of the procedure, tissue at a different spatial location will also require removal, in turn requiring that the spatial position of the cutting window be altered or rotated. Once again, with conventional surgical cutting instruments, this procedural specification requires the surgeon to physically change the orientation of the handpiece, thus taxing the surgeon's hand(s) and/or requiring the surgeon to temporarily halt the procedure and move to a different physical position relative to the patient.

Where the surgical cutting instrument is used in conjunction with an image guided surgery (IGS) system, additional concerns may arise. In particular, IGS generally entails registering the cutting window/cutting tip once deployed to the target site. Where the cutting window spatial orientation must be changed during the procedure, surgeons will commonly remove the instrument from the patient to more easily re-orientate the handpiece and thus the cutting window. When this is done, and following reinsertion of the cutting instrument, the cutting window/cutting tip must be re-registered relative to the IGS system, thereby extending the surgical procedure time.

The need to remove the surgical cutting instrument during a surgical procedure to effectuate a change in the cutting window spatial orientation is routinely encountered where the surgical cutting instrument includes one or more bends along a longitudinal length thereof. As a point of reference, some surgical cutting instruments, and in particular the outer tubular member thereof, are straight or linear along their longitudinal length. Others are curved in accordance with a specific procedure to facilitate positioning of the cutting tip against expected target site tissue. With the curved or bent configuration, the cutting window will move in an irregular fashion with rotation of the handpiece, effectively rotating about the bend or longitudinal point of curvature. Under these circumstances, then, it is virtually impossible for the surgeon to accurately alter the cutting window position without first removing the surgical cutting instrument from the patient.

Surgical cutting instruments continue to be extremely useful. However, the inability to readily and conveniently change a rotational orientation of the cutting window at the target site has not been fully addressed. Therefore, a need exists for a surgical cutting instrument capable of effectuating rotation of the cutting window relative to the handpiece operation with minimal impact on user visibility.

SUMMARY

Some aspects in accordance with principles of the present disclosure relate to a surgical cutting instrument including a first tubular member, a second tubular member, a sleeve member, a third sleeve member, and an orientation member. The first tubular member has a proximal section, an intermediate section, and a distal section. The distal section includes a cutting tip. The second tubular member has a proximal region, an intermediate region, and a distal region. The distal region forms a cutting window. The first elongated member is co-axially disposed within the second tubular member such that the cutting tip is selectively exposed at the cutting window. The sleeve member has a proximal end and a distal end. The first and second tubular members are co-axially disposed within the sleeve member. The third tubular member is co-axially disposed around the intermediate section of the first tubular member, the intermediate region of the second tubular member and the sleeve member. The orientation member is rotatable to transmit a rotational force applied to the orientation member to selectively rotate the second and third tubular members relative to the sleeve to effectuate spatial rotation of the cutting window.

Other aspects in accordance with principles of the present disclosure relate to a surgical cutting implement including a first tubular member, a second tubular member, a sleeve member, a hub assembly, and an orientation member. The first tubular member has a proximal section, an intermediate section, and a distal section, wherein the distal section includes a cutting tip. The second tubular member has a proximal region, an intermediate region, and a distal region. The distal region forms a cutting window. The first elongated member is co-axially disposed within the second tubular member such that the cutting tip is selectively exposed at the cutting window. The sleeve member has a proximal end, a distal end, and an intermediate portion between the proximal end and distal end. The first and second tubular members are co-axially disposed within the sleeve member. The second tubular member is selectively rotatable within the hub assembly. A hub of the hub assembly is rigidly secured to the sleeve member. The orientation member has a proximal end and a distal end. The orientation member is frictionally fit over the sleeve member at its proximal end and rigidly secured to the second tubular member. The orientation member is rotatable to transmit a rotational force applied to the orientation member to rotate the second tubular member relative to the hub to effectuate spatial rotation of the cutting window.

Other aspects in accordance with principles of the present disclosure relate to a method of using a surgical cutting instrument including grasping the surgical cutting instrument. The instrument includes a first tubular member, a second tubular member, a sleeve member, a hub assembly, and an orientation member. The first tubular member has a cutting tip. The second tubular member has a cutting window. The first tubular member is co-axially disposed within the second tubular member such that the cutting tip is selectively exposed at the cutting window. The first and second tubular members are co-axially disposed within the sleeve member. The second tubular member is selectively rotatable within the hub assembly. The hub assembly is rigidly secured to the sleeve member. The orientation member is frictionally fit over the sleeve member and rigidly secured to the third tubular member. The orientation hub is rotatable to transmit a rotational force applied to the orientation member to rotate the second tubular member relative to the hub assembly to effectuate spatial rotation of the cutting window. The method further includes positioning the cutting window and cutting tip at a target tissue, rotating the cutting tip to selectively cut the target tissue in a first area, maintaining the cutting tip at the target tissue, and rotating the orientation hub to selectively reposition the cutting window to expose the cutting tip to cut the target tissue in a second area.

DETAILED DESCRIPTION

Figure 1:
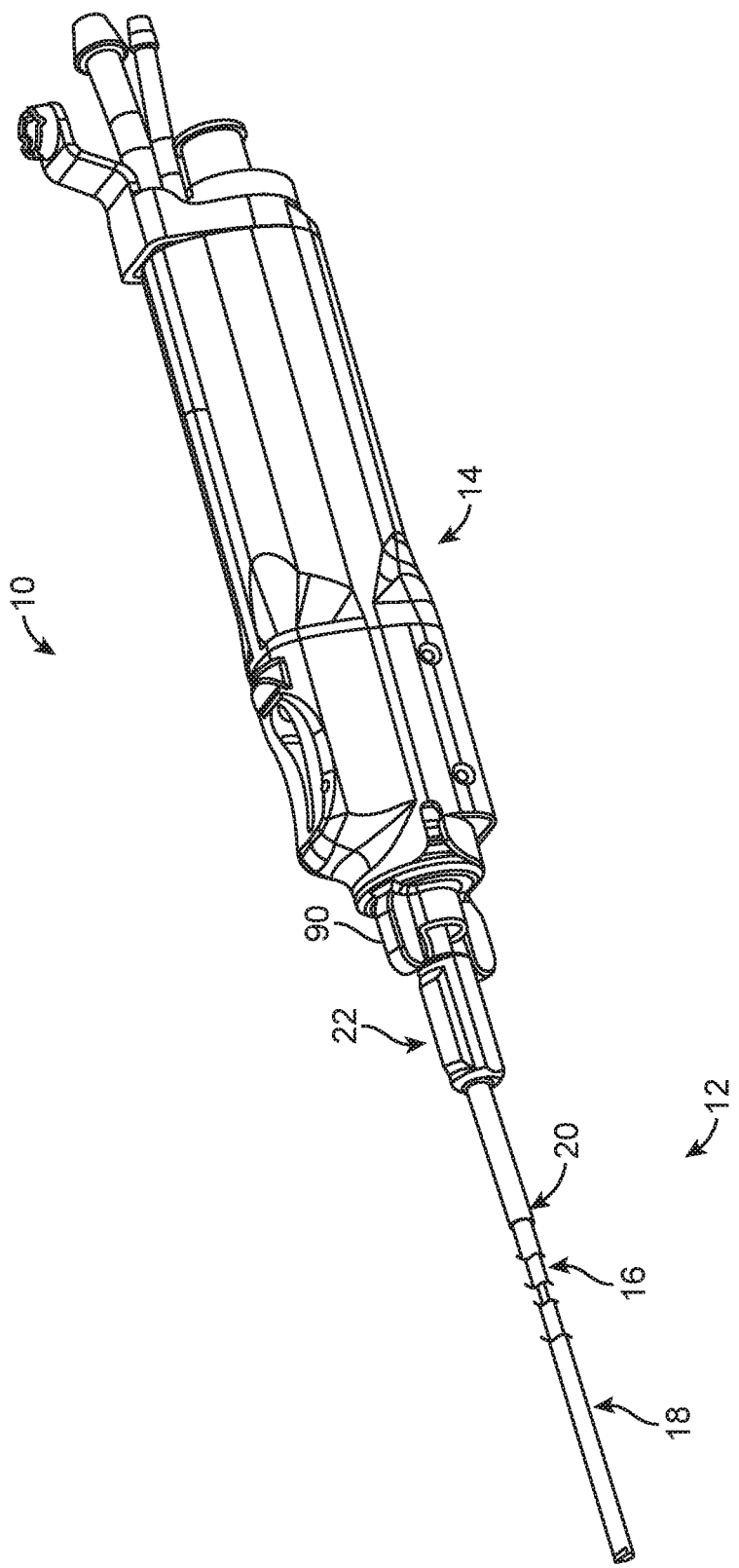
FIG. 1 is a perspective view of a surgical cutting instrument including a cutting blade assembly for surgically removing tissue in accordance with principles of the present disclosure.

One embodiment of a surgical cutting instrument 10 is illustrated in FIG. 1. The surgical cutting instrument 10 includes a cutting blade assembly 12 and a handpiece 14 (referenced generally in FIG. 1). The components are described in greater detail below. In general terms, however, the cutting blade assembly 12 includes a first tubular member 16, a second tubular member 18, a sleeve member 20, a third tubular member 21, and an orientation member 22.

Figure 2:
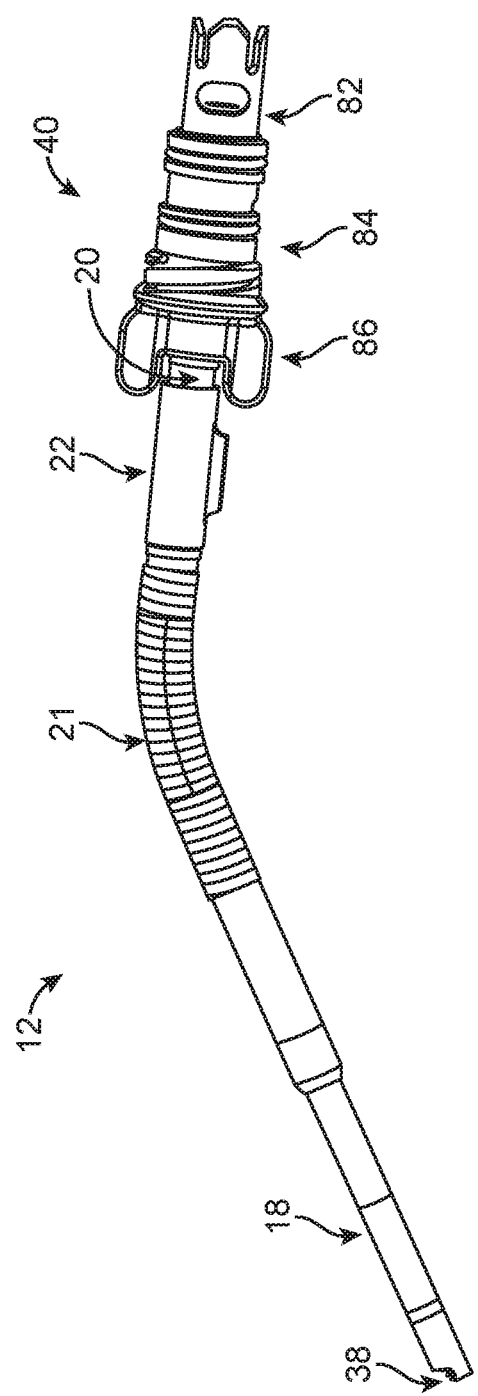
FIG. 2 is an enlarged side view of a cutting blade assembly according to one embodiment.
Figure 3:
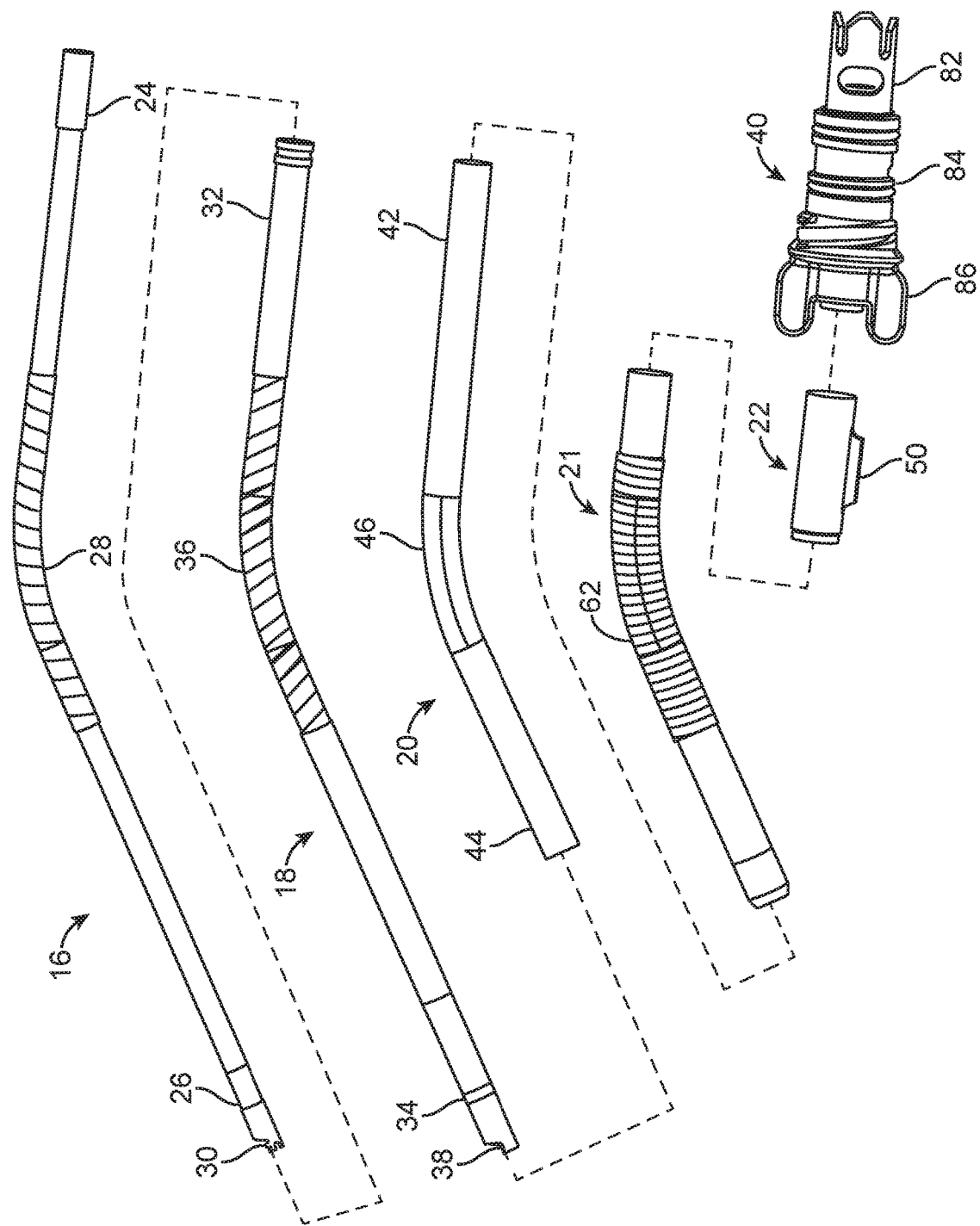
FIG. 3 is an exploded view of the cutting blade assembly of FIG. 2.

FIGS. 2 and 3 illustrate one embodiment of a cutting blade assembly 12 in accordance with the present disclosure useful with the surgical cutting instrument 10. The first tubular member 16 includes a proximal section 24, a distal section 26, and an intermediate section 28 extending between the proximal section 24 and the distal section 26. The distal section 26 forms a cutting tip 30. The second tubular member 18 includes a proximal region 32, a distal region 34, and an intermediate region 36 extending between the proximal region 32 and the distal region 34. The distal region 34 forms a cutting window 38. The first tubular member 16 is co-axially disposed within the second tubular member 18 such that the cutting tip 30 is exposed at the cutting window 38. A hub assembly 40 (see, e.g., FIG. 2) couples the first and second tubular members 16, 18, respectively, to the handpiece 14 such that the tubular members 16, 18 are rotatable relative to one another and the handpiece 14. In this regard, the sleeve member 20 and the orientation member 22 facilitate rotation of the second tubular member 18, and thus the cutting window 38, relative to the handpiece 14 as described in greater detail below.

The first tubular member 16 defines a lumen between an open proximal end and a distal end, the distal end having an opening therein communicating with the pathway/lumen and forming a suction inlet through which cut bodily tissue can be aspirated. The inner and outer surfaces of the first tubular member 16 are generally smooth and free from burs. The first tubular member 16 has a length such that an aspiration pathway may extend continuously through the hub assembly 40 of both the first and second tubular members 16, 18. In particular, the first tubular member 16 is coaxially disposed within the second tubular member 18 such that the distal region 34 of the second tubular member 18 is proximal to the distal section of the first tubular member 16.

The first tubular member 16 is an elongated tubular body and terminates at the distal cutting tip 30 formed in the distal section 26. The first tubular member 16 may oscillate or rotate in a single direction, as suitable for the procedure being performed. The cutting tip 30 is any cutting tip suitable for the desired surgical procedure. The proximal, intermediate, and distal sections 24, 26, 28 of the first tubular member 16 can be machined separately and assembled together. In one embodiment, at least a portion of the proximal section 24 of the first tubular member 16 is textured to include a raised fine diamond knurl.

The second tubular member 18 is an elongated tubular body defining a central lumen extending between a proximal end and a distal end. The central lumen of the second tubular member 18 generally defines uniform inside diameter and is generally uniformly smooth. An outer diameter of the second tubular member 18 can be greater at the proximal region 32 than at the distal region 34 for increased stability. The proximal region 32 of the second tubular member 18 includes radially projecting rings spaced apart to accommodate an o-ring disposable in between the radially projecting rings. When assembled, the first tubular member 16 is maintained within the central lumen of the second tubular member 18 such that an outer surface of the first tubular member 16 and an inner surface of the second tubular member 18 define an irrigation pathway to the cutting window 38. The central lumen of the second tubular member 18 is sized to accommodate the first tubular member 16 coaxially within and maintain the irrigation pathway between walls of the first and second tubular members 16, 18.

The sleeve member 20 has a proximal portion 42, a distal portion 44, and an intermediate portion 46 extending between the proximal portion 42 and the distal portion 44. The inner diameter of the sleeve member 20 is sized appropriately to accommodate the second tubular member 18 within. The proximal portion 42 can have an inner diameter larger than the remainder of the sleeve member 20 in order to accommodate the radial rings at the proximal region 32 of the second tubular member 18.

The third tubular member 21 includes a flexible portion 62. When assembled, the flexible portion 62 is longitudinally aligned with a flexible intermediate section 28 of the first tubular member 16, a flexible intermediate region 36 of the second tubular member 18, and a curved intermediate portion of the sleeve member 20.

Figure 4:
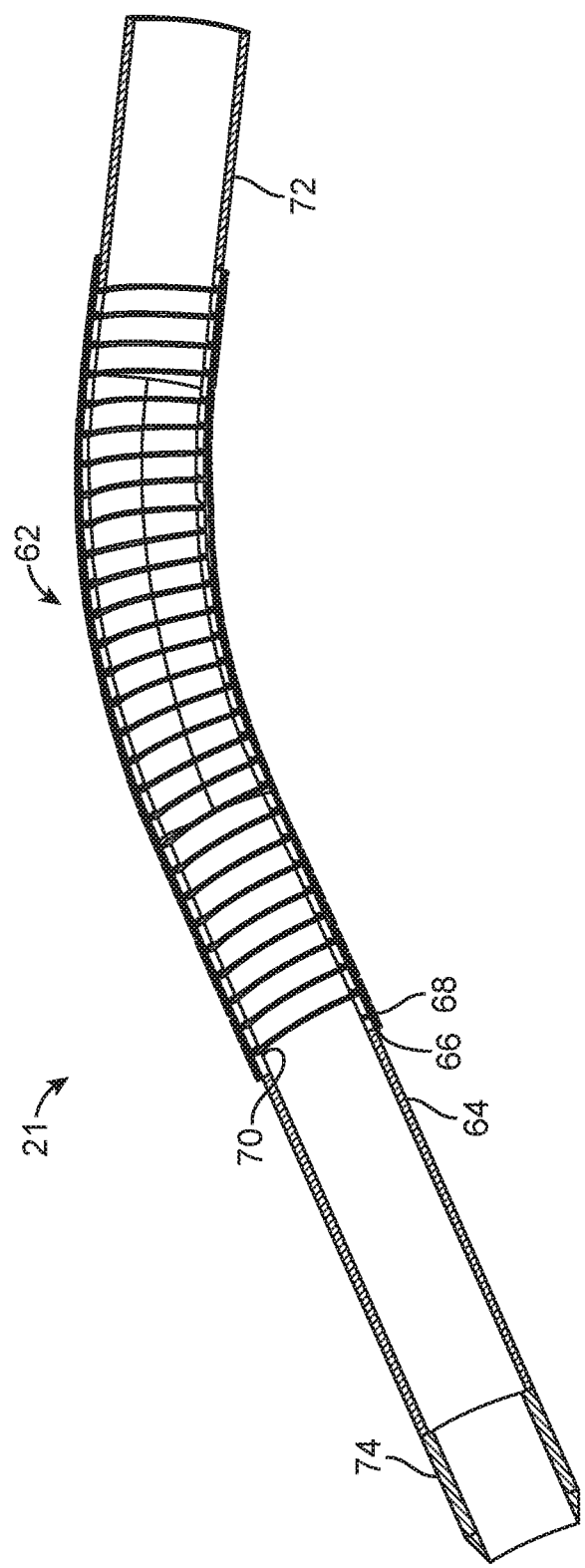
FIG. 4 is an enlarged cross-section view of the sleeve member of FIGS. 2 and 3.

As further illustrated in FIG. 4, the third tubular member 21 includes a tube body 64 and first and second flexible layers 66, 68. The tube body 64 includes a flexible intermediate section 70 positioned between a proximal section 72 and a distal section 74. The proximal and distal sections 72, 74 are rigid. The third tubular member 21 can be stainless steel or other suitable material. The first and second flexible layers 66, 68 can be spiral cut in opposite directions (i.e., left and right). The intermediate section 70 can also be spiral cut for uniform flexibility. The distal section 74 has a tapered end.

The window orientation member 22 is disposed along the second tubular member 18 distal to the hub assembly 40. The orientation member 22 can be adhesively or otherwise attached to the second tubular member 18 in order that the orientation member 22 and the second tubular member 18 can be rotated together as a unit. With additional reference to FIGS. 5A-5B, the orientation member 22 includes a directional indicator 50. When assembled, the directional indicator 50 of the orientation member 22 is aligned with the cutting window 38 of the second tubular member 18 in order that the user can selectively rotate and re-align the orientation member 22, and consequently, the cutting window 38 to face and be open toward the desired tissue to be removed.

Figure 5A:
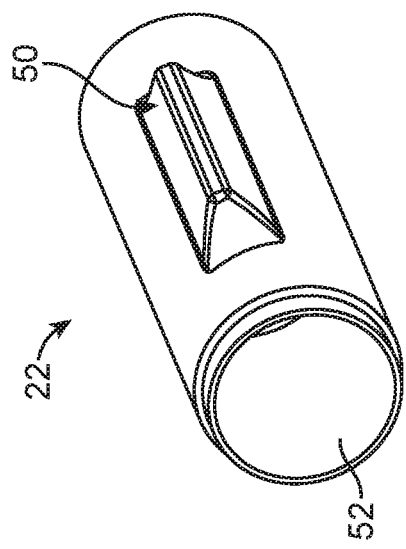
FIGS. 5A and 5B are enlarged prospective and cross-sectional views of the orientation member of FIGS. 2 and 3.
Figure 5B:
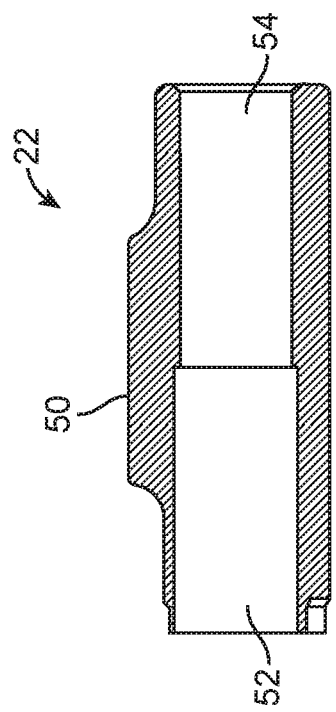

FIGS. 5A and 5B illustrate one embodiment of the orientation member 22 useful with the cutting blade assembly 12. The orientation member 22 has a generally tubular interior. The orientation member 22 includes a distal portion 52 and a proximal portion 54. The distal portion 52 has an inner diameter sized to suitable receive the third tubular member 21. The proximal portion 54 has an inner diameter sized to receive the sleeve member 20 and can have an inner diameter that is smaller than the distal portion 52. When assembled, the third tubular member 21 terminates within the distal portion 52 and the sleeve member 20 extends through the proximal portion 54. The terminal end of the proximal portion 54 can be beveled to ease insertion and assembly of the sleeve member 20 within proximal portion 54. The terminal end of the distal portion 52 can have a tapered outer surface to facilitate bonding with the third tubular member 21. The distal portion 52 of the orientation member 22 can be bonded with the third tubular member 21 with Loctite®, induction bonding, laser welding or other suitable bonding. In one embodiment, the orientation member 22 exerts inward radial force to prevent inadvertent rotation of the third tubular member 21 (and, in turn, the second tubular member 18 bonded to the third tubular member 21). An exterior surface of the orientation member 22 is easily gripped by a surgeon to manually change direction of the cutting window 38 at the distal end of the second tube 18. The orientation member 22 only rotates in response to suitable torque applied by the surgeon. The directional indicator 50 can protrude radially from the orientation member 22. The protruding indicator 50 is aligned with the cutting window 38 to provide visual and tactile feedback. In one embodiment, the directional indicator 50 includes audible and tactile feedback to indicate changes in the cutting window 38 orientation. In one embodiment, the orientation member 22 provides for separate and discrete changes in the orientation of the cutting window 38. In one embodiment, the orientation member 22 can allow the cutting window 38 to be oriented in any rotational direction desired by the surgeon.

Figure 6A:
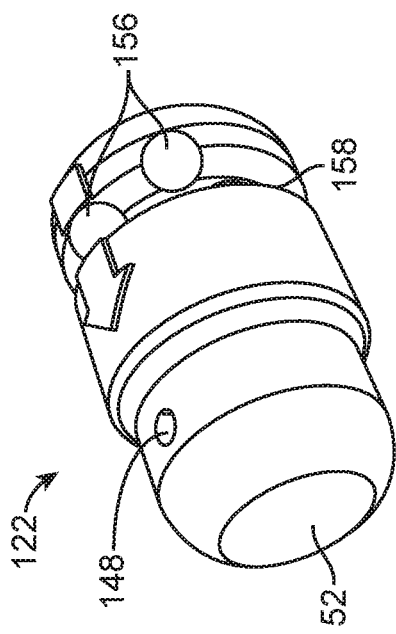
FIGS. 6A and 6B are enlarged prospective and cross-sectional views of another embodiment of an orientation member in accordance with aspects of this disclosure.
Figure 6B:
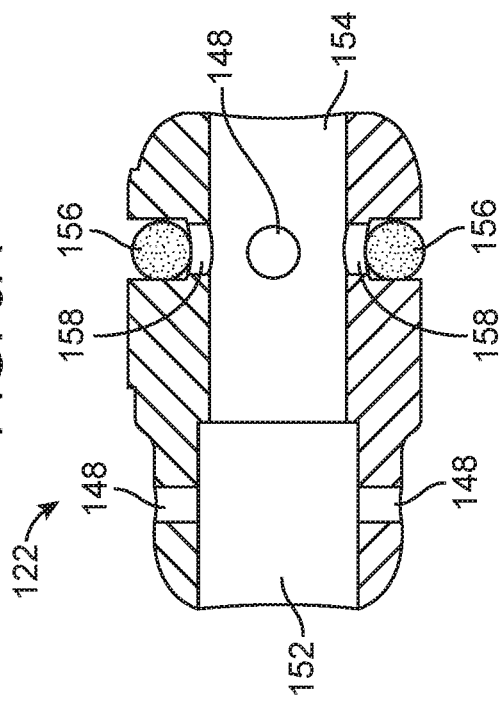

FIGS. 6A and 6B illustrate another embodiment of an orientation member 122 useful with the cutting blade assembly 12. The orientation member 122 has a generally tubular interior. The orientation member 122 includes a distal portion 152 and a proximal portion 154. The distal portion 152 has an inner diameter sized to suitable receive the third tubular member 21. The proximal portion 154 has an inner diameter sized to receive the sleeve member 20 and can have an inner diameter that is smaller than the distal portion 152. When assembled, the third tubular member 21 terminates within the distal portion 152 and the sleeve member 20 extends through the proximal portion 154. The terminal end of the proximal portion 154 can be beveled to ease insertion and assembly of the sleeve 20 within proximal portion 154. The terminal end of the distal portion 152 can have a tapered outer surface to facilitate bonding with the third tubular member 21. The distal portion 152 of the orientation member 122 can be bonded with the third tubular member 21 with Loctite®, induction bonding, laser welding or other suitable bonding. In one embodiment, weep ports 148 are included for adhesive bonding. In one embodiment, the orientation member 122 is a compliant member that exerts inward radial force to prevent inadvertent rotation of the third tubular member 21 (and, in turn, the second tubular member 18 bonded to the third tubular member 21). In one embodiment, the orientation member 122 includes balls 156 are disposed in a groove 158. When assembled, the balls 156 are mate with recesses in the sleeve member 20 (not shown). In another embodiment, the orientation member 122 includes a recess on a distal end to accommodate a ball and spring détente (not shown). An exterior surface of the orientation member 122 is easily gripped by a surgeon to manually change direction of the cutting window 38. The orientation member 122 only rotates in response to suitable torque applied by the surgeon. The directional indicator 150 can protrude linearly along an exterior of the orientation member 122. In one embodiment, the directional indicator is formed as an arrow to provide visual and tactile feedback. The protruding indicator 50 is aligned with the cutting window 38. In one embodiment, the directional indicator 150 includes audible and tactile feedback to indicate changes in the cutting window 38 orientation. In one embodiment, the orientation member 122 provides for separate and discrete changes in the orientation of the cutting window 38. For example, the orientation member 122 can allow the cutting window 38 to be reoriented in 90 degree increments. Other degrees of adjusted orientation are also suitable including free adjustment to any rotational direction.

With returning reference to FIG. 2, the first and second tubular members 16, 18 and the sleeve member 20 are proximally supported by the hub assembly 40. The orientation member 22 is positioned adjacent the hub assembly 40 for ease of manipulation by the surgeon and to ensure that the orientation member 22 does not hinder the surgeon's viewing of the cutting tip 30. The orientation member 22, or orientation hub 22, enables the user to selectively change the rotational orientation of the cutting window 16 without changing the position of the distal region 34 of the second tubular member 18 and the orientation of the sleeve member with respect to an x-axis. As a result, the surgeon can maintain the surgical instrument 10 in an essentially fixed position while changing the angle of attack of the cutting tip 30 by rotating the second tubular member 18.

The intermediate regions 28, 36, of the tubular members 16, 18, respectively, are flexible. The intermediate section 28 and the intermediate region 36 are aligned and assembled coaxially along a length of the cutting blade assembly 12. The section 28 and the region 36 can accept a curvature imposed by the intermediate portion 46 of the sleeve member 20 and transmit torque applied at the hub assembly 40 to the cutting tip 30 to rotate the cutting tip 30 with sufficient force to sever tissue or other body material exposed through the cutting window 38. The second tubular member 18 includes a flexible intermediate region 36 that envelopes the intermediate section of the first tubular member 16 and allows the user to rotate the second tubular member 18 with respect to the hub assembly 40 by manipulating the orientation member 22.

In one embodiment, the first and second tubular members 16, 18 are metal, such as stainless steel. Similar to the first tubular member 16, the second tubular member 18 has rigid proximal and distal regions 32, 34 with the flexible intermediate region 36 disposed between regions 32, 34. The intermediate section 28 can be spiral cut to provide uniform flexibility and efficiently transmit torque (i.e., rotational force) applied at the proximal section 24 of the first tubular member 16 to the distal section 26 through any curvature imposed by the intermediate portion 46 of the sleeve member 20. The intermediate section 28 can be either left or right slanted spiral cut. The intermediate region 36 and the intermediate section 28 are oppositely spiral cut. For example, the intermediate region 36 is left slanted spiral cut and the intermediate section 28 is right slanted spiral cut, allowing the cutting blade assembly 12 to rotate in either direction without compromising the structural integrity of the cutting blade assembly 12.

With reference to FIGS. 2 and 3, the hub assembly 40 includes a first hub assembly 82, a second hub assembly 84, and a fastener 86. As described below, the first hub assembly 82 maintains the first tubular member 16 and facilitates connection of the first tubular member 16 to the motor (not shown). The second hub assembly 50 includes a dynamic seal 88 and an outer hub 90. The second tubular member 18 extends distally from within the outer hub 90. With reference to FIG. 1, the fastener 90 removably secures the hub assemblies 82, 84 within the handpiece 14. The second hub assembly 84 can assume a wide variety of forms suitable for the surgical cutting instrument 10.

The first tubular member 16 is assembled with the second tubular member 18 and the assembled hubs 82, 84 are coaxially received within the handpiece 14 (not shown), with the first and second tubular members 16, 18 extending distal the hub assemblies 82, 84. The inner hub assembly 82 and the outer hub assembly 84 cooperate to facilitate the rotational relationship of the first tubular member 16 and the second tubular member 18. The handpiece 14 supports both the inner blade assembly 16 and the outer blade assembly first tubular member 16 and the second tubular member 18. Rotation of the first tubular member 16 is translated to the cutting tip 30 to effect selectively removing the target tissue at the treatment site, as described in greater detail below. With this construction, aspirated liquids and solids (not shown) can be delivered from the cutting tip 30 through the lumen of the first tubular member 16 via a sealed pathway. Other constructions capable of effectuating flow of irrigation liquid to the second tubular member 18 and aspiration through the first tubular member 16 are also envisioned.

Figure 7:
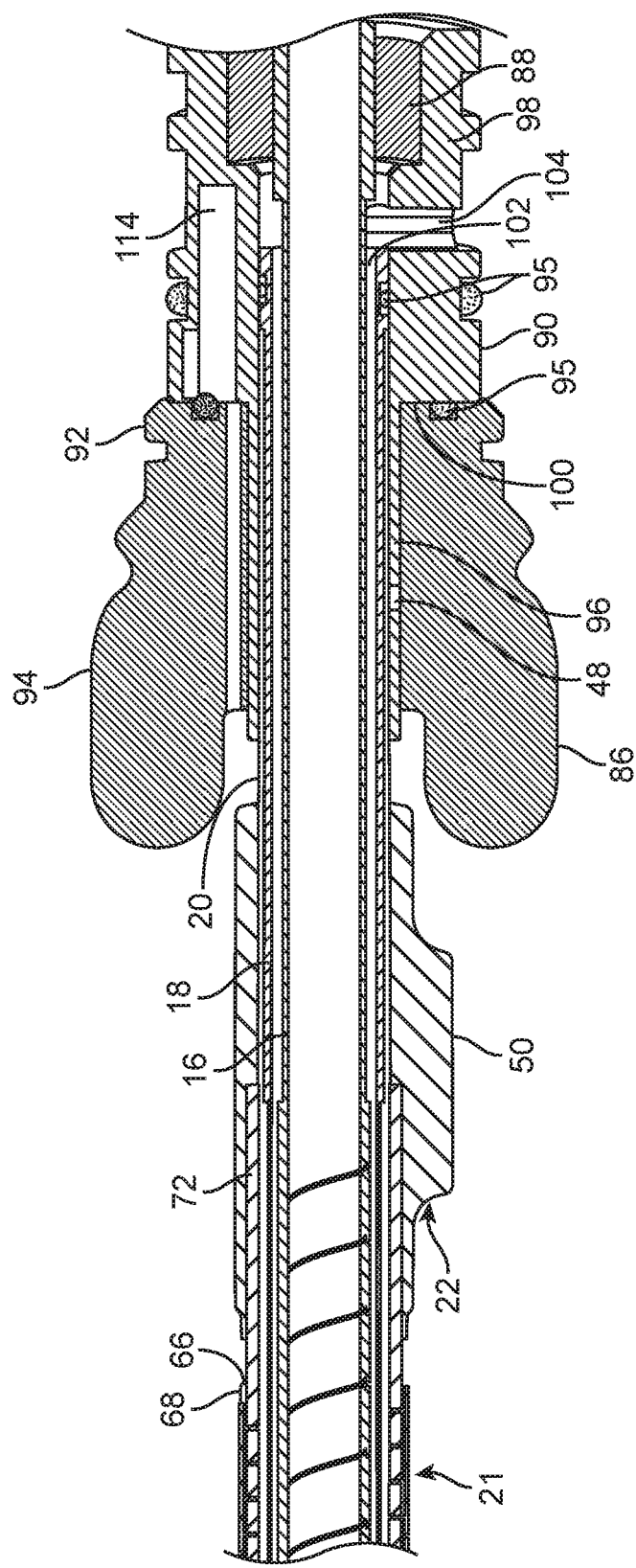
FIG. 7 is an enlarged cross-sectional view of a proximal region of the cutting blade assembly of FIG. 2 in accordance with principles of the present disclosure.

With reference to FIG. 7, the fastener 86 includes winged tabs 94 extending distally away from the threads 92 as well as radially outward. The winged tabs 94 are configured for ease of handling and turning the threads 92 of the fastener 86 to engage or disengage the cutting blade assembly 12 to or from the handpiece 14 (see, e.g., FIG. 1). In this manner, the fastener 86 is removably secured to the outer hub assembly 84 within the handpiece 14 (i.e., threads 92 are mate-able with threads in the handpiece, not shown). Other engagement and disengagement mechanisms are also acceptable. In one embodiment, two winged tabs 94 are included and are disposed on opposing sides of the fastener 86. Other quantities and configurations of winged tabs 94 can also be suitable. In one embodiment, threads 92 are provided to allow the fastener 86 to be turned 180° when securing within the handpiece 14. Sufficient threads 92 are included to prevent the fastener 86 from inadvertently disengaging from the handpiece 14 when the surgical cutting instrument 10 is in use. In any regard, suitable threads 92 are provided to secure the outer hub assembly 84, and the cutting blade assembly 12, to the handpiece 14 until a user rotates the fastener 86 by rotationally pushing against the winged tabs 94 to disengage the threads 92 from the handpiece 14. In one embodiment, a circumferential notch is included at a proximal end. An o-ring 95 is insertable into the circumferential notch and is disposed against to the outer hub 90 when assembled and can reduce or absorb some of the vibrations, particularly in an axial direction, of the cutting instrument 10 during operation.

The outer hub 90 includes a neck 96 and a base 98. A radial shoulder 100 is defined between the neck 96 and the base 98 and radially extends from an outer diameter of the neck 96 to an outer diameter of the base 98. The neck 96 is sized and configured to extend within and through the fastener 86. A passageway 102 extends through the neck 96 and the base 98. The irrigation inlet 104 extends from an exterior surface of the outer hub 84 and fluidly connects with the passageway 102. In one embodiment, the passageway 102 extends along the longitudinal axis of the hub assembly 40 and the irrigation inlet 104 extends perpendicularly to the exterior surface of the outer hub 84. In accordance with aspects of the disclosure, the irrigation inlet 104 is disposed within the handpiece 14 to fluidly connect to the fluid pathway and irrigation port when assembled to the handpiece 14.

The second tubular member 18 extends within the passageway 102 and terminates distal to the irrigation inlet 104 such that the irrigation inlet 104 freely communicates with the lumen of the second tubular member 118. The sleeve member 20 extends distally from within the outer hub assembly 84. In particular, the sleeve member 20 extends coaxially around the second tubular member 18 and terminates within the outer hub 84. A proximal end of the sleeve member 20 terminates approximately flush with the proximal end of the proximal region 32 of the second tubular member 18. A seal ring 95 is disposed between the radial rings formed on the proximal region 32 of the second tubular member 18 to facilitate a fluid tight seal between the proximal region 32 of the second tubular member 18 and the sleeve member 20. The sleeve member 20 can be adhesively attached within the outer hub 84. At least one glue weep port 48 extends at an angle to, and in some cases perpendicular, to the longitudinal axis extending along a length of the passageway 102. The at least one adhesive weep port 106 directly and fluidly connects to the passageway 102 and is also fluidly open at an exterior surface of the outer hub 84. Adhesive (not shown), when used to adhere the sleeve member 20 within the passageway 102 of the outer hub 90, is inserted in the distal end after or with insertion of the sleeve member 20 and excess adhesive can exit the neck 96 at least one adhesive weep port 48 during assembly.

With continued reference to FIG. 7, the first tubular member 16 extends beyond the proximal end of the second tubular member 18 and through the dynamic seal 88 disposed at the proximal end portion of the outer hub 90 to connect with the inner hub assembly 82 (not shown). The dynamic seal 88 fluidly seals around the first tubular member 16. In addition, as described in greater detail below, the outer surface of the outer hub 90 is adapted to receive seal rings 95 (e.g., o-rings) on either side (i.e., proximal and distal) of an irrigation inlet 104 to effectuate a fluid-tight seal between the outer hub 90 and the handpiece 14 (not shown). As assembled, the seal rings 95 can also provide radial vibration attenuation, thereby reducing vibration at the cutting tip 30. In some embodiments, the dynamic seal 88 and the seal rings 95 are a polytetrafluoroethylene (PTFE) material such as Teflon®, although other suitable materials are also acceptable.

In one embodiment, the outer hub 90 includes an identification port 114. The identification port 114 is configured to accept a radio-frequency identification device (RFID). The RFID includes data to identify the size and blade type, for example, of the cutting implement 10 that is transferred to an integrated power-console (IPC) when the cutting implement 10 is assembled with the handpiece 14. The IPC (not shown), upon receiving information from the RFID, can supply power to operate the cutting instrument 10 at a suitable speed as well as fluid and aspiration suitable for the specific cutting instrument 10. Other cutting implement identification systems, such as magnetic hall sensors, for example, are also acceptable.

With further reference to FIG. 7, the proximal section 72 of the third tubular member 21 extends into a distal end of the orientation member 22 and is fixedly attached to the orientation member 22 with adhesive or other appropriate means. The distal end of the third tubular member 21 is adhered to the second tubular member 18. The distal end of the sleeve member 20 maintains a frictional relationship to the second tubular member 18 and the orientation member 22. As discussed above, the sleeve member 20 is adhered to the outer hub 90. Manual rotation of the orientation member 22 facilitates rotation of the third and second tubular members 21, 18 and the cutting window 38.

Upon final assembly, the cutting tip 30 is positioned at the cutting window 38 with the two components being rotatable relative to one another as discussed above. As the first tubular member 16 is rotatably driven at its proximal end, for example by the motorized handpiece 14, the surface or edge of the cutting tip 30 will cooperate with the cutting window 38 in the second tubular member 18 to shear, cut, or shave the tissue. As assembled, the outside surface of the first tubular member 16 is coated with a biocompatible tungsten-carbide/carbon coating to prevent galling and decrease friction between first and second tubular members 16, 18. Micro-machining such as electrical discharge machining (EDM), electrochemical machining (ECM), mechanical machining, chemical machining, micro-electromechanical system (MEMS) processing, or other suitable micro-machining method can be used to form the first and second tubular members 16, 18, in particular, the cutting tip 30 and cutting window 38. In one embodiment, the distal region 34 is laser beam welded to the remainder of the second tubular member 18 and the distal section 26 is laser beam welded to the intermediate section 28 of the first tubular member 16.

As illustrated in FIG. 2, the sleeve member 20 is curved, or bent, in an intermediate portion 46 to angularly offset cutting tip 30. The curved intermediate region 46 enables surgical instrument 10 to operate on surgical areas that are difficult to otherwise reach with a straight instrument. With additional reference to FIG. 7, the rigid, stationary sleeve member 20 is coaxially disposed around the second tubular member 18 and first tubular member 16.

The surgical cutting instrument 10 is highly useful in the surgical treatment (i.e., removal) of intracranial and spinal tumors (as well as possibly other surgical procedures). In this regard, treatment of a tumor in accordance with aspects of the present disclosure includes forming an access opening in the patient's skull (e.g., a conventional craniotomy). Once a target site at which the brain tumor has been exposed, the system 10 is operated to remove at least some, preferably all, of the brain tumor, regardless of whether it is a soft or a fibrous tumor.

Once the surgeon positions the distal portion 44 adjacent the tumor, the surgeon manipulates the handpiece 14 and/or the orientation member 22, 122 so as to position the cutting window 38 adjacent and/or into the brain tumor. The curve, or bend, of the cutting blade assembly 12 defined by the curved sleeve member 20 facilitates the surgeon's hand and the handpiece 14 remaining out of the field of view of the microscope and aids in visualization of the procedure. Rotation of the first tubular member 16 of the cutting instrument 10 is effectuated by activation through the IPC (not shown). The controller/IPC (via a connection between the handpiece 14) enables selective rotational control over the first tubular member 16 to cause high-speed rotation of the cutting instrument 10 for debriding or otherwise cutting the target tissue. Depending upon the particular location of the tumor, the cutting implement 10 can be manipulated sideways across the tumor or downward without overtly twisting/contortion of the surgeon's hand(s).

In one embodiment, the window orientation member can be manually manipulated to orient the cutting window in any radial direction. Frictional engagement of the orientation member 22 with the sleeve member 20 holds the cutting window 38 in place until suitable rotational pressure is applied by the user to reorient the window orientation member 22, and thus, the cutting window 38. One of the surgeon's hands grasps a base portion of the handpiece 14, whereas the surgeon's other hand grasps the orientation member 22 that is otherwise affixed to the second tubular member 18 (and thus the cutting window 38). Once properly held, the surgeon then applies a torque to the orientation member 22 by forcibly rotating his/her hands.

Although the present disclosure has been described with reference to preferred embodiments, workers skilled in the art will recognize that changes can be made in form and detail without departing from the spirit and scope of the present disclosure.

What is claimed is:

1. A surgical cutting instrument comprising:
    a first tubular member having a proximal section, an intermediate section, and a distal section, wherein the distal section includes a cutting tip;
    a second tubular member having a proximal region, an intermediate region, and a distal region, wherein the distal region forms a cutting window, wherein the first tubular member is co-axially disposed within the second tubular member such that the cutting tip is selectively exposed at the cutting window;
    a sleeve member having a proximal end and a distal end, wherein the first and second tubular members are co-axially disposed within the sleeve member;
    a third tubular member co-axially disposed around the intermediate section of the first tubular member, the intermediate region of the second tubular member and the sleeve member; and
    an orientation member rotatable to transmit a rotational force applied to the orientation member to selectively rotate the second and third tubular members relative to the sleeve member to effectuate spatial rotation of the cutting window.

2. The surgical cutting instrument of claim 1, wherein the sleeve member is rigid.

3. The surgical cutting instrument of claim 1, wherein the intermediate section of the first tubular member and the intermediate region of the second tubular member are flexible.

4. The surgical cutting instrument of claim 1, wherein the third tubular member has a rigid distal section, a rigid proximal section, and a flexible portion between the rigid distal end and the rigid proximal end.

5. The surgical cutting instrument of claim 1, wherein the sleeve member has an intermediate portion between the proximal end and the distal end, and wherein the intermediate portion is rigidly curved.

6. The surgical cutting instrument of claim 5, wherein the intermediate section of the first tubular member and the intermediate region of the second tubular member are longitudinally aligned with the intermediate portion of the sleeve member.

7. The surgical cutting instrument of claim 6, wherein an intermediate portion of the third tubular member is longitudinally aligned to overlap the intermediate section of the first tubular member, the intermediate region of the second tubular member, and the intermediate portion of the sleeve member.

8. The surgical cutting instrument of claim 1, wherein the third tubular member is selectively rotatable with respect to the sleeve member, wherein the orientation member is fixedly secured to the proximal section of the third tubular member and the distal section of the third tubular member is fixedly secured to the distal region of the second tubular member, wherein a rotational force applied to the orientation member rotates the third and second tubular members.

9. A surgical cutting instrument, comprising:
    a first tubular member having a cutting tip;
    a second tubular member having a cutting window, wherein the first tubular member is co-axially disposed within the second tubular member such that the cutting tip is selectively exposed at the cutting window;
    a sleeve member, wherein the first and second tubular members are co-axially disposed within the sleeve member;
    a third tubular member, wherein the sleeve member is co-axially disposed within the third tubular member, and wherein the third tubular member is rigidly secured to the second tubular member; and
    an orientation member having a proximal portion and a distal portion, wherein the orientation member is frictionally fit over the sleeve member at the proximal portion and rigidly secured to the third tubular member at the distal portion, wherein the orientation member is rotatable to transmit a rotational force applied to the orientation member to rotate the second tubular member relative to the sleeve member to effectuate spatial rotation of the cutting window.

10. The surgical cutting instrument of claim 9, wherein a proximal portion of the sleeve member extends distally through the proximal portion of the orientation member.

11. The surgical cutting instrument of claim 9, wherein a proximal section of the third tubular member terminates within the orientation member.

12. The surgical cutting instrument of claim 9, wherein an intermediate portion of the third tubular member is co-axially disposed around an intermediate section of the first tubular member, an intermediate region of the second tubular member and a curved portion of the sleeve member.

13. The surgical cutting instrument of claim 12, wherein the intermediate portion, the intermediate section, and intermediate region are flexible.

14. The surgical cutting instrument of claim 12, wherein the intermediate section of the first tubular member and the intermediate region of the second tubular member are spiral cut.

15. The surgical cutting instrument of claim 12, further comprising:
    a first hub mounted to a proximal section of the first tubular member;
    a second hub mounted to a proximal region of the second tubular member and a proximal end of the sleeve member,
    wherein the proximal end of the sleeve member is fixedly secured to the second hub.

16. The surgical cutting instrument of claim 9, wherein the third tubular member includes an intermediate tube body between a proximal section and a distal section, wherein the intermediate tube body includes first and second flexible layers.

17. The surgical cutting instrument of claim 16, wherein the first and second flexible layers are spiral cut in opposite directions.

* * * * *